United States Patent [19]

Cline et al.

[11] Patent Number: 4,879,668

[45] Date of Patent: Nov. 7, 1989

[54] METHOD OF DISPLAYING INTERNAL SURFACES OF THREE-DIMENSIONAL MEDICAL IMAGES

[75] Inventors: Harvey E. Cline, Schenectady; Siegwalt Ludke, Scotia; William E. Lorensen, Ballston Lake, all of N.Y.

[73] Assignee: General Electric Company, Schenectady, N.Y.

[21] Appl. No.: 943,357

[22] Filed: Dec. 19, 1986

[51] Int. Cl.$^4$ .............................................. G06F 15/42
[52] U.S. Cl. .............................. 364/522; 364/413.18; 364/413.19; 364/413.22
[58] Field of Search ............... 364/518, 521, 522, 414, 364/415, 413, 518, 521, 522, 413.16, 413.18, 413.19, 413.22; 378/4, 901

[56] References Cited

U.S. PATENT DOCUMENTS

| | | | |
|---|---|---|---|
| 4,105,922 | 8/1978 | Lambert et al. | 364/414 |
| 4,117,336 | 9/1978 | Bates | 364/414 X |
| 4,475,104 | 10/1984 | Shen | 340/729 |
| 4,641,351 | 2/1987 | Preston, Jr. | 364/414 X |
| 4,674,046 | 6/1987 | Ozeki et al. | 364/522 X |
| 4,694,404 | 9/1987 | Meagher | 364/518 |
| 4,710,876 | 12/1987 | Cline et al. | 364/414 |
| 4,719,585 | 1/1988 | Cline et al. | 364/518 |
| 4,729,098 | 3/1988 | Cline et al. | 364/414 |
| 4,751,643 | 6/1988 | Lorensen et al. | 364/413.13 |

OTHER PUBLICATIONS

James D. Foley et al., "Fundamentals of Interactive Computer Graphics", Addison-Wesley Publishing Company, pp. 446–450.

J. Lawrence Paul, "Three Dimensional Display of Objects from Planar Contours", *Graphics Interface '83*, pp. 129–131.

Machover, C. and Myers, W., "Interactive Computer Graphics", *Computer Magazine*, IEEE Computer Society Publication, (Oct. 1984), pp. 145–161.

Ehud Artzy et al., "The Theory, Design, Implementation and Evaluation of a Three-Dimensional Surface Detection Algorithm", *Computer and Image Processing*, vol. 15 (1981), pp. 1–24.

H. E. Cline et al., "Computer Aided Surface Reconstruction of Interference Contours", *Applied Optics*, vol. 21, No. 24, Dec. 15, 1982, pp. 4481–4488.

Primary Examiner—Gary V. Harkcom
Assistant Examiner—Mark K. Zimmerman
Attorney, Agent, or Firm—Geoffrey H. Krauss; James C. Davis, Jr.; Marvin Snyder

[57] ABSTRACT

A count is kept of the number of surfaces traversed, in a variety of three-dimensional imaging systems which are particularly advantageous for use in medical applications based upon data generated by magnetic resonance imaging systems and computerized axial tomographic imaging systems. The system is particularly advantageous in a surgical workstation for planning a wide variety of operative procedures. Surfaces may be selected and displayed simultaneously so as to provide the viewer with a significantly improved knowledge of the relationship of various internal body structures.

8 Claims, 2 Drawing Sheets

METHOD OF DISPLAYING INTERNAL SURFACES OF THREE-DIMENSIONAL MEDICAL IMAGES

BACKGROUND OF THE INVENTION

The present invention is generally directed to a system and method for displaying surface information! More particularly, the present invention is directed to a system and method for displaying internal surfaces existing at various depths and locations within a three-dimensional body. The images of the surfaces displayed are typically contained within the interior regions of solid bodies which are examined by computed axial tomographic (CAT) x-ray systems or by nuclear magnetic resonance (NMR) imaging systems either of which is capable of generating three-dimensional arrays of data representative of one or more physical properties at various locations within a three-dimensional object. The images generated in the practice of the present invention are particularly useful in that they provide three-dimensional data for examination by physicians, radiologists and other medical practitioners.

In conventional x-ray systems, a two-dimensional shadow image is created based upon the different x-ray absorption characteristics of bone and soft tissues. A great improvement on the conventional x-ray system as a diagnostic tool is provided by computed axial tomographic systems, which have been developed over the last ten years or so. These so-called CAT systems are x-ray based and initially were used to produce single two-dimensional views depicting transverse slices of a body, object or patient. Three dimensional information was thereafter gleaned from CAT scan data by generating data for a number of contiguous slices and using the inferential abilities of a radiologist to suggest a three-dimensional representation for the various internal organs. In the present invention, shaded and contoured three-dimensional images are generated from the three-dimensional array of data generated by a sequence of such contiguous CAT scans or magnetic resonance imaging scans. The newer magnetic resonance imaging technology possesses the capability to better discriminate between various tissue types, not just between bone and soft tissue and therefore offers the capability for producing more discriminating images in many situations. NMR imaging systems are also capable of generating physiological data rather than just image data. However, whether NMR or CAT systems are employed, data has generally been available only as a sequence of slices, and systems have not generally been available which provide shaded two-dimensional images which accurately depict true three-dimensional views.

Prior work by at least one of the inventors herein has significantly solved some of the major problems associated with the production of high resolution three-dimensional medical images. In particular, a system referred to as "marching cubes" was disclosed in application Ser. No. 741,390 filed June 5, 1985 and now U.S. Pat. No. 4,710,876, issued Dec. 1, 1987. An additional application relating to the display of three-dimensional images and a system referred to as "dividing cubes" was disclosed in application, Ser. No. 770,164 filed on Aug. 28, 1985 and now U.S. Pat. No. 4,719,585, issued Jan. 12, 1988 incorporated herein by reference. At the time of invention, all of the individuals in the present case and these other cases were under an obligation of assignment to the assignee of the present application. Both of these applications are assigned to the same assignee as the present invention. The present invention is in fact applicable to processing either in accordance with the marching cubes system or the dividing cubes system or in accordance with other similar systems.

Attention is now directed to the specific problem solved by the system of the present invention. In the display of three-dimensional images, and more particularly in the display of medical images, one often encounters three-dimensional objects having multiple internal surfaces which occur in layers. For example, three-dimensional data associated with physical measurements of the human head produce data associated with the skin, with the skull, the brain, nasal cavities and various internal soft tissue structures. In a three-dimensional view of the head, for example, there are circumstances in which it would be desirable to be able to effectively strip away skin tissue so as to observe underlying bone tissue. Likewise, there are situations in which it would be desirable to be able to peel away both skin and bone surfaces to reveal underlying structures such as the brain. While the methods of marching cubes and dividing cubes are capable of displaying selected tissues such as all bone or all skin or all brain tissue, it is nonetheless desirable to be able to display selected portions of these structures and/or to simultaneously display them on the same screen so as to more clearly indicate their relationship. This is particularly advantageous as a surgical planning method since it is capable of showing the relationship between various bodily structures. It is noted, however, that while the present invention is particularly directed to the medical imaging arts, there is nothing contained herein which would limit its use thereto. Any three-dimensional measurement process carried out on an object having an internal structure is amenable to processing in accordance with the system of the present invention.

An image of the anatomy typically consists of the visible surfaces of tissues computed by scanning the data and projecting surface patches onto a view plane. In a three-dimensional array of data, the volume element is called a voxel, in an analogy with that of the area element which is referred to as a pixel in two-dimensional situations. In certain other dimensional algorithms, voxel size limited the resolution of three-dimensional reconstructions resulting in images that appear block-like or stepped as compared to having the smooth surfaces of real tissues. Attempts to produce smoother images by averaging over the neighboring voxels however, actually tended to reduce the resolution of the image. Other methods for three-dimensional display generation of images have been based upon measurement of the distance from an imaginary observation point to a patch on the surface of the object and on the estimated surface normal of the patch.

To shade the surface of a three-dimensional image projected onto a view plane, an intensity is calculated from the component of the unit normal vector parallel to the view direction. Surfaces parallel to the view plane are fully illuminated, while those at oblique angles to the view plane are gray and surfaces perpendicular to the view plane are dark or black. The marching cubes and dividing cubes systems estimate the surface normal direction from a gradient vector of the three-dimensional density function. This is a useful estimate since the gradient is perpendicular to surfaces of constant density. Consequently, the gradient vector is parallel to the unit surface normal vector. The unit normal vector is calculated by normalizing the gradient vector at the surface of interest. In the dividing cubes system, the gradient vector defined at each lattice point is linearly interpolated over the voxel to given a local value of the gradient vector at the desired surface. The unit surface normal is the gradient vector divided by its magnitude. Similar variations of the normal direction is also employable in the marching cubes system. The surface that results appears smooth because the interpolated gradient vector continuously varies with the distance across a voxel boundary. This form of gradient shading is preferably employed in both the marching cubes and dividing cubes systems

SUMMARY OF THE INVENTION

In accordance with a preferred embodiment of the present invention, a system for the display of the internal surfaces of three-dimensional objects employs a surface counter and scans the three-dimensional data from a single direction. A count of the number of surfaces crossed is made during the scanning process. One or more threshold values are used to isolate selected surfaces for viewing. The surface counter provides a signal which is indicative of the particular surface or surfaces of interest. In one embodiment of the present invention, the signal is used to directly label the units of information supplied to the display processor with an indication of the particular surface to which the unit pertains. In particular, in a system employing the dividing cubes method, the coordinate and normal register (or registers) may be provided with an additional information block to indicate that it belongs to a particular surface. Likewise, in the marching cubes system, the signal from the surface counter may be appended to information provided by the polygon generator or interpolator so as to provide a surface label which is appended to the polygon list information supplied to the display processor. Alternatively, information from the surface number counter may be supplied directly to the display processor for storage in one or more buffers contained therein. In this embodiment, the display or image may be recalled from one or more buffers selected in accordance with the surface number count. Alternatively, the single buffer in the display processor may contain individualized surface count information so that only select buffer locations are employed in the image generation.

Accordingly, it is seen that it is an object of the present invention to provide a system and method for the display of three-dimensional information.

It is a further object of the present invention to provide a display system for use in conjunction with CAT scanners, ultrasound devices, NMR imaging systems and any and all other systems capable of generating three-dimensional data representative of one or more physical properties within a body to be studied.

It is yet another object of the present invention to provide a graphical system for medical image display which is capable of interactive use and yet at the same time produces high quality images providing textural, shading and other visual clues to the user.

It is yet another object of the present invention to provide a three-dimensional graphics display system which is compatible with current CAD/CAM systems.

Another object of the present invention is the generation and display of three-dimensional raster format based information.

Still another object of the present invention is to maximize the information contained in a three-dimensional data array for the purpose of surface representation.

It is also an object of the present invention to provide a system and method which is readily fabricatable in conventional electronic hardware, especially that used in CAD/CAM systems.

It is yet another object of the present invention to provide medical practitioners with the ability to emulate surgical procedures graphically prior to undertaking invasive measures.

Additionally, it is an object of the present invention to provide a plurality of three-dimensional surface views from a single set of collected data.

It is a still further object of the present invention to provide a system and method for the display of selected internal surface structures of a three-dimensional body.

It is yet another object of the present invention to provide a method and system which permits a medical practitioner to graphically peel away select tissue surfaces from a three-dimensional view of a solid body displayed on a two-dimensional surface.

Lastly, but not limited hereto, it is an object of the present invention to provide a system and method for the display of three-dimensional images of internal surface structures in such a way that the specific viewing angle and cross-sectional viewing plane may be selected by the user in an interactive manner.

DESCRIPTION OF THE FIGURES

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

DETAILED DESCRIPTION OF THE INVENTION

Figure 1:
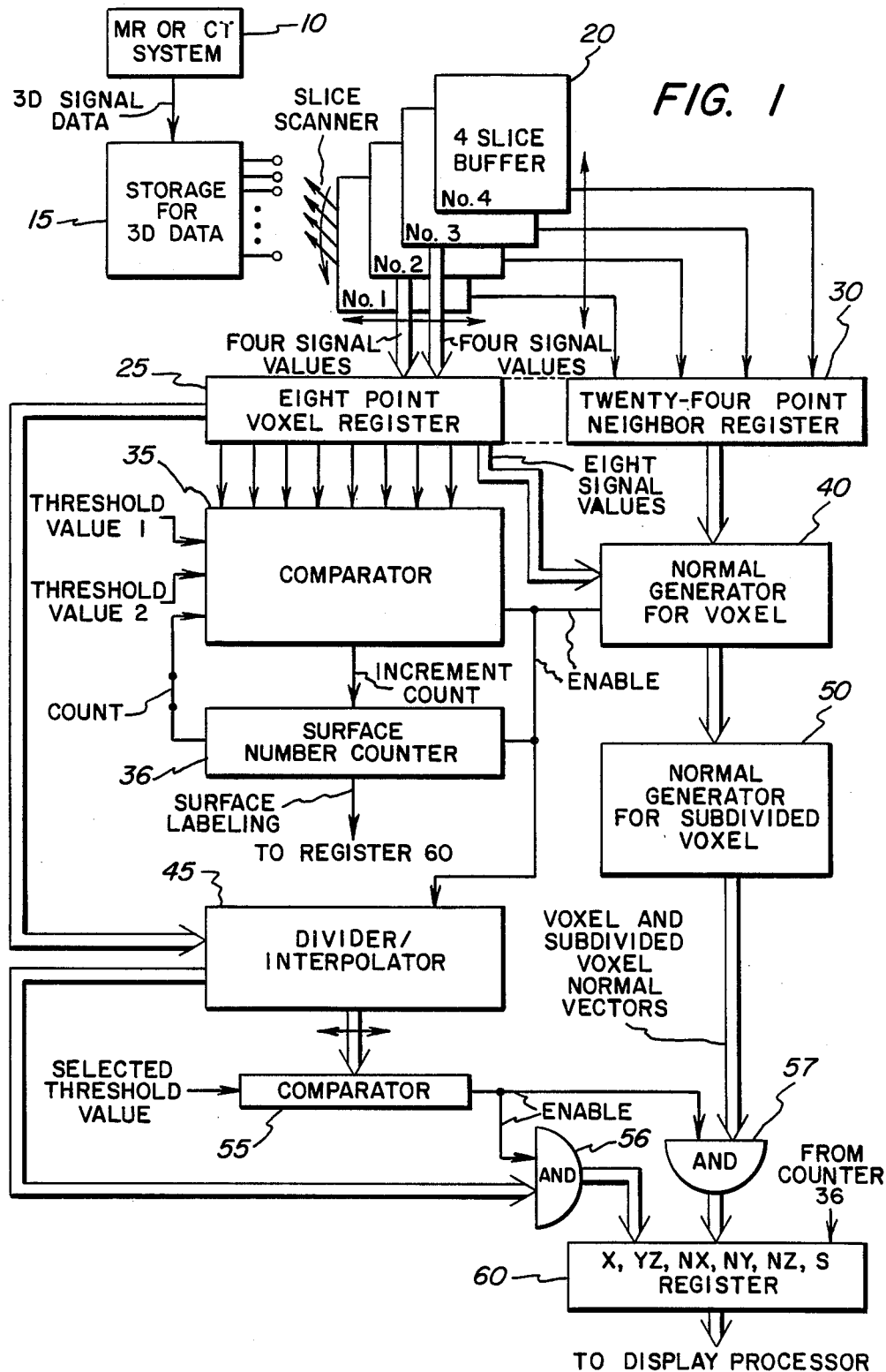
FIG. 1 is a schematic diagram illustrating the apparatus and method of the present invention in the context of a "dividing cubes" processing system.
Figure 2:
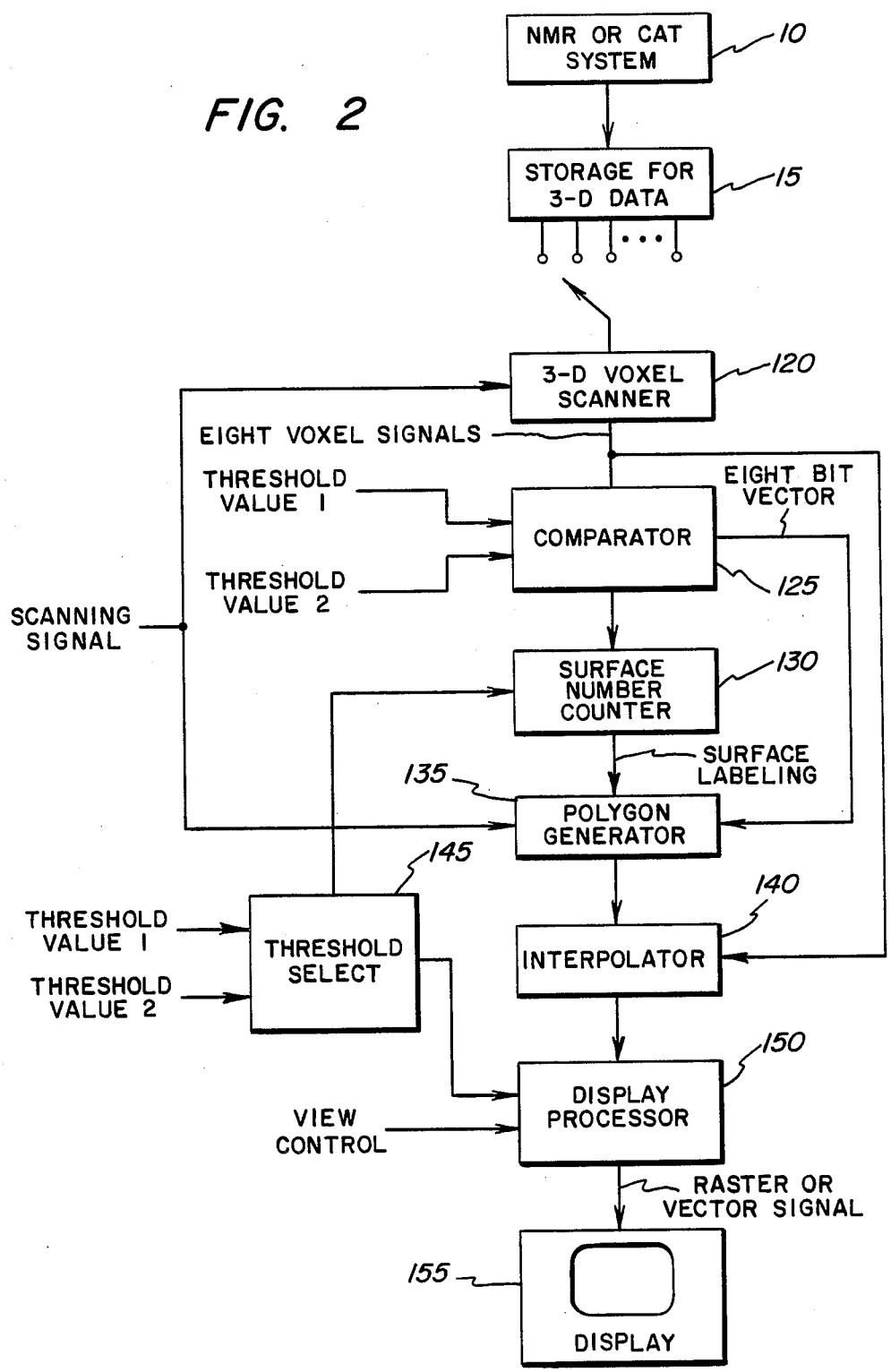
FIG. 2 is a schematic diagram illustrating the method and apparatus of the present invention in the context of its use in a "marching cubes" system.

In any embodiment of the present invention, the essential features are that the three-dimensional data is scanned from a single direction and means are provided for counting the number of surfaces crossed as determined by one or more threshold values. As each surface is crossed, the counter is updated. Typically, the counter includes from one to three bits of information. However, it is noted that it is also possible to employ a "counter" in which the surface number is coded directly in terms of a bit position. For example, rather than coding the third surface encountered with the binary number "11" in a two bit register, it is instead possible to code this information by turning bit position 3 to the on-state in a four bit register with bit positions 0 through 3. The essence of this labeling process is thus indicated as one in which means are provided for labeling various surfaces as they are encountered in scanning the three-dimensional data array. Accordingly, surface counting may be employed in any system and method for the display of three-dimensional graphic information on a two-dimensional screen. For purposes of illustration, however, the surface counting method is particularly described herein for the marching cubes and dividing cubes systems referred to above. FIG. 1 illustrates the surface counting method employed in a dividing cubes system and FIG. 2 illustrates this same method employed in a marching cubes system. The former system is considered first.

In particular, in a method and apparatus of the present invention relating to a dividing cubes system, a sequence of voxel elements is examined. In a preferred embodiment, data from four consecutive MR or CT scan slices is analyzed at a time. The reason for the desirability of employing four slices of data is that each voxel element (with its eight grid locations and) with the 24 grid locations which are cubically adjacent to it, occupy a position in four adjacent slices. In this voxel and grid location arrangement, the "cubic" voxel itself lies in two adjacent slices and is sandwiched between two other adjacent slices on either side of it. These slices are arranged in an order so as to be traversed sequentially in the scan direction. Associated with each vertex point is a signal pattern value which represents a measurement of at least one physical property which is associated with a three-dimensional body at regularly spaced grid locations within the body. Thus, there is no requirement that the voxel elements herein form cubic structures. It is sufficient that they form regularly spaced parallelopiped type structures. The grid locations define volume elements or voxels. For the practice of the dividing cubes aspects of the present invention, each voxel vertex is also associated with the three adjacent grid locations (referred to herein as additional grid locations) as described above. These adjacent or additional grid locations are the ones which lie along grid coordinate lines and which are not specifically included in the voxel itself. There are 24 such grid locations, as described above. In the dividing cubes system, the data values at these additional grid locations are employed, along with the data values at the voxel vertex locations, to generate the data values which represent normal vectors associated with each voxel vertex. The various normal vector components are computed using finite difference methods, for example, a central difference. Data from four adjacent slices is employed to generate normal vectors associated with each voxel vertex location. The resulting vector formed from differences may then be scaled to unit magnitude. However, it is noted below that it is possible to employ vectors, which while initially normalized to a unit status, may be further adjusted to provide texture information on certain plane cuts.

FIG. 1 illustrates, in schematic form, a flow chart and hardware description of a system in accordance with one embodiment of the present invention. Three-dimensional-signal data is provided from NMR or CT scan system 10 (for example). This data is typically stored in an appropriate storage system 15. Typically, this storage system comprises some form of magnetic storage medium such as a floppy disk, hard disk drive or tape. The data is organized in a format which permits associating each physical measurement representation with a corresponding grid location associated with that measurement.

In a preferred embodiment of a dividing cubes system which employs the present invention, a 4-slice buffer 20 is employed. This buffer employs layers No. 1, No. 2, No. 3 and No. 4 with each memory layer containing representations for the signal pattern values at the various grid locations. Each layer preferably contains the data for an entire two-dimensional slice of the body being imaged. A slice scanner is employed so as to scan through the data along a single direction, such as along one of the grid axis directions. In preferred embodiments of the present invention, there is direct correlation between buffer address values and the grid locations within the body as described above. It should be borne in mind that as one scans through the data in one axis direction by means of the slice scanner, it is only necessary to retrieve a single additional slice of information at a time. In short, the scanner can be made to operate in a fashion so that only data from a single image plane need be retrieved at one time. As indicated in FIG. 2 of the hereinabove referred-to application 770, 164 (now U.S. Pat. No. 4,719,585) and substantially duplicated in FIG. 1 hereof, additional scanning is performed throughout layers No. 2 and No. 3 of buffer 20. It is these intermediate layers which contain grid locations at voxel vertices. Four signal values from one voxel face are provided from layer 2 and at the same time, four signal values from layer 3 are similarly provided to voxel register 25. The four signal values from layer No. 3, of course, correspond to the four vertices opposite the voxel slice selected from layer No. 2. Thus, each voxel element is defined by four grid locations from layer No. 2 and four grid locations from layer No. 3 of buffer 20. As indicated by the horizontal double-headed arrows on the flowpath lines from layers No. 2 and No. 3 to register 25, the operation of the present invention proceeds from voxel to voxel by means of scanning operations carried out in layers No. 2 and No. 3. Corresponding to the selection of each voxel element, a total of eight values is therefore supplied to voxel register 25. At the same time, 24 additional measurements are provided to voxel neighbor register 30. Dotted lines are shown connecting registers 25 and 30 to indicate that in practice these registers might actually comprise a single 32 cell register. Each cell in the register contains the corresponding physical measurement in an appropriate and consistent representational format. In this way, for each voxel element, the values associated with voxel vertices are supplied to register 25. In a like fashion, the physical measurement values associated with the 24 additional grid locations are supplied to register 30.

Each of the eight voxel signal values from register 25 are supplied to comparator 35. Comparator 35 operates to compare each of the eight values supplied with one or moreuser-supplied threshold values. From each of the threshold values, if all of the eight comparison results are the same, then it is clear that the surface selected for one of the threshold values does not pass through the particular voxel being scanned. In this case, the enable line inhibits the output generation for that voxel. This enable inhibition function may also be supplied to surface number counter 36 although it is not strictly necessary to do so. If any of the comparisons generated by comparator 35 are different than the other comparisons, then normal vector generation is enabled.

Furthermore, each time a comparison results in a selection, a signal is sent to surface number counter 36 if the results of the comparison indicate that a new surface has been encountered. For example, if two thresholds are provided to comparator 35, it can be established that the voxel being examined intersects a surface defined by one threshold value, but does not intersect a surface defined by another threshold value which may be greater or lesser. In this way, surface number counter 36 may be set to indicate that threshold value 1 has already been crossed indicating, for example, that scanning has already progressed through facial tissue. Further indications that the voxel being examined does not intersect facial tissue, but instead lies inside a surface of bone tissue is determined from the contents of surface number counter 36 and the threshold value or values supplied to comparator 35. In this way, surface number counter 36 contains coded information indicating a count of the number of distinct surfaces which have been encountered. Surface number counter 36 is therefore seen to provide a count or label associated with each intersected voxel vertex. It is clear that it is not necessary to provide labeling information for voxels which do not intersect any surface. This latter function may be indicated using the enable line from comparator 35.

The effect of these operations is also considered with respect to the orientation of a view plane selected by the user. A view plane is determined by the view direction selected by the user. For example, through the user's selection of a sequential plurality of different view planes, the object can be made to rotate. Such rotations are also capable of being generated by rotating the data in the coordinate system of the object being viewed. These are well-understood operations commonly practiced in the electronics graphic display arts.

The view plane possesses a (unit) normal vector associated with it. For purposes of establishing a convention herein, it may be assumed that this normal is oriented toward the object. Thus this normal vector can lie in any of the eight octants, as determined by a coordinate system fixed with respect to the body. During scanning of the data for purposes of determining intersections of surfaces of constant value, the three-coordinate locations are preferably varied in response to the selection of a view plane (or equivalently, the view plane normal, as defined above). For example, selection of a particular view plane would specify that scanning is to take place from a particular "side of the data" and progress in a single coordinate direction.

In accordance with a particular embodiment of the present invention, the voxels that are found to be intersecting selected surface structures are projected back onto the view plane and a count is made of the number of such voxels associated with pixel elements on the view plane. Depth (buffer) information is employed in this method to prevent these counts from being associated with the backsides of surface structures. What is a backside structure is determined from the view plane selected and the concomitantly selected data-scanning direction. In accordance with the count values, the second surface may therefore be selected for display.

In addition to selection of a view plane, the user may also select a cut plane. A cut plane is a plane that "cuts through the body" to provide the user with a sectional view. Such surgical sectioning is, however, only carried out on the measured data. One method for creating the effect of a cut plane on the display is simply to eliminate data (or to selectively accept presented data) that falls on one side of the cut plane. Typically, although not necessarily, the removed data corresponds to measured values existing between the cut plane and the view plane. This also permits images of internal bodily structures. When a cut plane is employed, data scanning is performed essentially as described above. However, rather than recording surface count information, depth from the view plane is determined and recorded for each view plane pixel. For initial consideration and ease of understanding, it is easier to consider the situation when the view plane and cut plane are parallel. The surface elements which are closest to the cut plane are displayed as long as they are behind the cut plane. In this case, there are still several possibilities with respect to the display of surface elements intersected by the cut plane. The surface elements on the cut plane may be treated as a monolithic two-dimensional solid and shaded in accordance with the surface normal direction associated with the cut plane. Alternatively, surface elements lying on the cut plane may be ignored so as to reveal internal surfaces. For example, part of the top of the skull may be removed by a cut plane and rather than showing the region inside the intersection of the plane and skull as a solid, as above, it is possible, using surface count information, to display the interior of the skull as viewed through the opening established by the cut plane. A third alternative with respect to the display of cut plane determined surfaces is the generation of textured information. Such information is obtained from interpolated data on the cut plane surface which is used to modulate the surface normal. This latter feature is particularly useful in situations in which the cut plane extends through relatively thick bone material whose internal marrow regions would not be seen if a solid intersection was shown. Texturing eliminates this problem. The particular form of texturing is not critical. It is merely necessary to provide some variation in surface normal direction across the cut surface in response to data values associated with voxel elements lying on the surface.

At this point, several alternative embodiments of the present invention are possible. All of these embodiments are nonetheless centered around the concept that the surface counter information is used to tag or label information supplied to the display processor. This information may be affixed to data as it is processed by the remainder of the system shown in FIG. 1 (below counter 36), or the information may be supplied to the display processor through output register 60, or it may be supplied directly to the display processor. In the latter case, it is typical that buffer memory in the display processor would include indicia, associated with each memory element, which is indicative of the surface number. This would permit the display processor to display those, and only those, data points associated with a particular surface. It is important here to keys in mind that the function of hidden pixel removal and/or hidden line removal is typically carried out by the display processor itself in accordance with well known computer graphics principles.

Apart from the distinctions described, the rest of the dividing cubes system shown operates in its prescribed manner. In particular, the generation of normal vectors is accomplished in functional block 40 which is provided with the eight signal values from voxel register 25 and the 24 additional signal values from neighbor register 30. When enabled for a given voxel element, normal generator 40 operates to produce eight normal vectors, each associated with a different one of the voxel vertices. This normal generation is accomplished by a differencing method involving the six signal values associated with adjacent voxel vertex elements. Although it is not necessary at this point in the process, normal generator 40 may also operate to adjust the magnitude of the normal vectors generated so that each possesses a unit magnitude.

It is noted that cuts are easily made possible simply by eliminating data on one side of a plane. This may also be done selectively by tissue type. Additionally, it is also noted that for tissues lying on one side of a cut plane and which have been eliminated from view as a result of selection of a particular surface, the texture of the cut surface may be indicated by modulating the surface normal vectors to provide shading and texture information. In this case, the vectors are all of magnitude less than one (or some selected value), but are nonetheless otherwise adjusted to indicate texture. For example, this feature is particularly useful in the display of certain medical images. For example, it may be decided, in accordance with the present invention, to view a human head from a given cut plane. That is to say, a cross-sectional view may be desired. However, it may be desired to show the brain in full. In such cases, the surface of the bone which lies on the cut plane may be shaded as pure white, for example, or may be provided with texture by modulating surface normals occurring along the bone cut. This provides a more realistic image and is capable of illustrating tissue information associated with regions inside of "cut" bones. Again, it should be pointed out that all of the "cutting" and "peeling away" of tissues described herein is done solely by graphical image processing devices and is totally non-invasive with respect to the patient. Moreover, it is done on data which need only be collected once in many cases.

An important function of the dividing cubes system is carried out by divider/interpolator 45. This operation is also enabled by the results of comparator 35. In particular, when a voxel is found which contains a segment of the surface defined by the threshold value or values, additional operations ar enabled. These additional generations generate data values associated with grid locations within a selected voxel element. Additionally, normal vectors are generated for each of these internal grid locations which are constructed by voxel subdivision and interpolation. For example, functional block 45 operates upon the eight signal values from register 25 to produce a set of additional interpolated measurement values, preferably (because of system complexity considerations) by linear interpolation. However, non-linear interpolation may also be employed. For example, the grid location midway between two voxel vertices may be assigned a measurement value equal to one-half the sum of the measurement values at the two adjacent voxel locations. In a like manner, a grid location which lies in the middle of a voxel face may be assigned a measurement value which is equal to one-fourth of the sum of the measurement values assigned to each of the vertex grid locations associated with that face. Similarly, a grid location contained within the center of a voxel element may be assigned a measurement value which is equal to one-eighth of the sum of the measurement values associated with all eight of the voxel data values. Thus, for each voxel selected, a subdivision operation occurs. It is noted that it is preferable to divide the voxel element into subdivisions along the various grid axes corresponding to the same power of two. For example, subdivision by a factor of one-half is common in the practice of the present invention. However, subdivision by other integers is also possible and it is also possible to employ different subdivision units in different coordinate (that is, grid axis) directions.

In exactly the same fashion as described above, normal generator 50 produces normal vectors associated within each of the grid locations with the subdivided voxel. For example, the normal vectors associated with an edge point between two voxel vertices is generated as one-half of the vector sum of the normal vectors associated with that particular edge. Analogous results are generated for additional normal vectors associated with cube faces and interiors. Functional block 50 also preferably operates to scale each of the normal vectors generated, to fix the magnitude of each vector generated at unity (or modulated as described above). Custom integrated circuit chips are available for performing such square root operations necessary for magnitude normalization of the vectors generated. (Note though that here normalization is used in two different senses, one to to describe the magnitude of the vector and another to indicate that the vector is at least approximately normal to a surface determined by the threshold value or values.) Accordingly, from each voxel selected as a result of the comparison performed by comparator 35, divider/interpolator 45 produces a set of interpolated measurement values corresponding to a more finely divided voxel element. In the same manner, normal generator 50 provides signal values representing normal vectors occurring in voxel vertices and also at intermediate and internal grid locations. For each selected voxel element, there is a fixed number of subvoxel elements generated. As suggested by the doubled-ended horizontal arrow between divider/interpolator 45 and comparator 55, each subvoxel is scanned and compared with the same threshold value as used in comparator 35. This comparison operation is performed by comparator 55 for each subvoxel element. Since, however, it is assumed that the same surface intersects the voxel as a subvoxel element, it is not necessary for divider/interpolator 45 or comparator 55 to employ surface count information, although this information might be supplied to these processing elements for ultimate transmission to register 60.

When comparisons with the threshold value supplied to comparator 55 are made with respect to a single subdivided volume element and when different comparison results are obtained for at least two of the eight comparisons made for that subdivided volume element, or subvoxel, an output of appropriate location and normal vector directions is made. In this fashion, the output of comparator 55 enables AND gates 56 and 57 to supply signal values to output register 60. Accordingly, for each selected subvoxel element within a selected voxel element, a set of grid location values x, y and z, together with the components of a normal vector nx. ny, nz at that location, are provided to register 60. Register 60 may also contain surface counts information. It is noted as above, that various embodiments of the present invention arise as a result of various signal path routings for surface count information.

As indicated above, the approach of surface number counting is also applicable to a marching cubes system. Such a system incorporating the present invention is illustrated in FIG. 2. In this illustrative system, eight voxel vertex signal pattern values are examined at one time in comparator 125. These voxel vertex signals are selected by three-dimensional voxel scanner 120. As above, the scan preferably proceeds from one planar slice to the next. Comparator 125 operates substantially as described above. However, in marching cubes system, a significant output of the comparator is an eight bit vector which acts as an index for a polygon generator table. A synchronizing scanning signal is applied to scanner 120 and polygon generator 135 so as to provide an indication of the specific grid locations for which each polygon or set of polygons is generated. Using the same method as described above, comparator 125 and surface counter 130 operate in conjunction with each other to provide surface labeling information for each polygon generated. As above, this labeled data is suppliable to display processor 150 through a number of possible signal paths. It is noted that the surface labeling signal from counter 130 to polygon generator 135 may be supplied directly to display 155, to interpolator 140 or to display processor 150. The essential aspect here is that the correspondence between surface (count) number and the associated triangle and normal be established and maintained.

From the above, it should be appreciated that the system and method of the present invention provides a mechanism for more selectively viewing shaded three-dimensional images of internal bodily structures as measured by such devices as magnetic resonance imaging machines and computerized axial tomography machines. It is further seen that appropriate selection of threshold values permits the viewer to choose surfaces to be ignored and surfaces to be displayed. It is noted that the system of the present invention also permits the simultaneous viewing of two or more surface structures on the same screen. This is particularly advantageous to medical practitioners who wish to determine the three-dimensional relationship between various bodily structures. Such systems are particularly advantageous as surgical planning workstations. It is also noted that the system and method of the present invention is capable of selecting various cut planes for viewing. It is further noted that many of the functions performed by the various parts of the system illustrated in FIGS. 1 and 2 may in fact be performed through the use of one or more general or special purpose digital computation systems. It is also noted that since the present invention is capable of displaying multiple tissue types, particularly from data generated from nuclear magnetic resonance imaging systems, it is also possible to employ color in the displayed image. Color selection is based upon surface count information, for example.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

The invention claimed is:

1. An apparatus for displaying three-dimensional structure surfaces, said apparatus comprising:
   means for storing three-dimensional signal patterns, each signal pattern containing a value of at least one physical property measured at each of regularly spaced three-dimensional grid locations within a three-dimensional body;
   means for sequentially and progressively scanning through said three-dimensional signal patterns in said storing means to retrieve those three-dimensional signal patterns associated with a preselective unidirectional sequence of said grid locations within said body;
   means for comparing each value of said retried signal patterns with at least one threshold value;
   counter means having an output which is set responsive to said comparing means indicating that a present value of the sequence of signal patterns has traversed across any one of said at least one threshold value, for labelling each surface traversed in the single direction of said unidirectional sequence;
   means for tessellating the output of said comparing means to generate polygonal surfaces which approximate an intersection of surfaces determined by said at least one threshold value; with voxel elements being defined by said grid;
   means for indicating, for each of said polygonal surfaces, surface depth information as determined by said counter means;
   display processor means receiving, from at least said tessellating means, the tessellated comparing means output and for converting said output to a display format; and
   means for displaying surfaces determined by said at least one threshold value, said displaying means being driven by said display processor means.

2. An apparatus for displaying three-dimensional structure surfaces, said apparatus comprising:
   means for storing three-dimensional signal patterns, each signal pattern containing a value of at least one physical property measured at each of regularly spaced three-dimensional grid locations, defining volume elements each shaped as a solid parallelopiped, within a three-dimensional body;
   means for sequentially and progressively scanning through the three-dimensional signal patterns in said storing means to retrieve those three-dimensional signal patterns associated with a preselected unidirectional sequence of said grid locations within said body;
   means for providing a unique set of three-dimensional coordinates associated with each particular one of said grid location;
   means for identifying, from a value of said signal patterns and from said associated three-dimensional grid location, those of said grid locations which lie adjacent to an associated one of at least one selected surface within said body;
   means, responsive to said identifying means, for indicating a number of surfaces traversed in the single direction of said unidirectional sequence;
   counter means, set by said surface number indicating means, for labelling each surface traversed in said single direction;
   means for generating a normal vector to one predeterminately selected side of said surface at each of said grid locations at which said surface is identified;
   means for associating surface counter information with said normal vectors; and
   display processor means receiving said associated surface count information an normal vectors for providing a shaded image representing at least one predetermined one of the at least one of the selected surface.

3. A method for displaying three-dimensional structure surfaces, comprising the steps of:
   storing three-dimensional surface patterns, each representative of a value of at least one physical property measured at each of a multiplicity of regularly spaced grid locations within a three-dimensional body;

sequentially and progressively scanning the three-dimensional signal patterns to retrieve those three-dimensional signal patterns associated with a preselected unidirectional sequence of grid locations within the body;

comparing the retrieved signal patterns with a threshold value selecting each of at least one surface to determine all intersections of a selected surface with each of a multiplicity of voxel elements each defined by a set of cubically-adjacent grid locations;

accumulating, for each pixel in a user-selected plane, a count of a number of surface intersections in a selected direction, normal to the body and from the view plane toward the body;

generating a vector approximating a normal to each of at least one selected surface for at least those of the grid locations associated with any voxel intersected by each of the at least one selected surface;

supplying each normal vector and its associated grid locations to a display processor; and displaying the at least one selected surface responsive to the normal vectors and the view plane counts.

4. The method of claim 3 in which more than one selected surface is displayed simultaneously.

5. The method of claim 3 further including the step of selecting for display those points lying on one side of a user-selected cut plane.

6. The method of claim 5 in which a normal vector, associated with each point in the cut plane where the cut plane intersects the body, is set equal to a vector normal to the cut plane.

7. The method of claim 5 in which the amplitude of each normal vector associated with the cut plane is modulated in response to the signal pattern value associated with the grid location for which the normal vector was generated, to cause a textured pattern to be provided on the cut plane.

8. The method of claim 5 in which internal structure surfaces are selected in response to the surface count information to cause internal surfaces of volume-defining slids to also be viewable.

* * * * *